(12) United States Patent
Cho et al.

(10) Patent No.: US 9,931,619 B2
(45) Date of Patent: Apr. 3, 2018

(54) ETHANOL DEHYDRATION CATALYST FOR ENERGY SAVING AND METHOD OF MANUFACTURING ETHYLENE USING SAME

(71) Applicant: LOTTE CHEMICAL CORPORATION, Seoul (KR)

(72) Inventors: Joungmo Cho, Daejeon (KR); In Ae Kim, Daejeon (KR); Jae Yeon Lee, Daejeon (KR); Seung Hee Kang, Daejeon (KR); Young Jong Seo, Daejeon (KR)

(73) Assignee: LOTTE CHEMICAL CORPORATION, Seoul (KR)

( * ) Notice: Subject to any disclaimer, the term of this patent is extended or adjusted under 35 U.S.C. 154(b) by 32 days.

(21) Appl. No.: 14/785,270

(22) PCT Filed: Apr. 14, 2014

(86) PCT No.: PCT/KR2014/003212
§ 371 (c)(1),
(2) Date: Oct. 16, 2015

(87) PCT Pub. No.: WO2014/171688
PCT Pub. Date: Oct. 23, 2014

(65) Prior Publication Data
US 2016/0074848 A1    Mar. 17, 2016

(30) Foreign Application Priority Data

Apr. 18, 2013 (KR) .................. 10-2013-0042846
Apr. 10, 2014 (KR) .................. 10-2014-0042722

(51) Int. Cl.
*B01J 29/06* (2006.01)
*B01J 29/40* (2006.01)
*C07C 1/24* (2006.01)
*B01J 37/28* (2006.01)
*B01J 37/02* (2006.01)

(52) U.S. Cl.
CPC ............. *B01J 29/405* (2013.01); *C07C 1/24* (2013.01); *B01J 37/0201* (2013.01); *B01J 37/28* (2013.01); *B01J 2229/186* (2013.01); *C07C 2529/40* (2013.01); *Y02P 20/52* (2015.11)

(58) Field of Classification Search
CPC ...... B01J 29/405; B01J 37/0201; B01J 37/28; B01J 2229/186
USPC .............................. 502/60, 73, 77
See application file for complete search history.

(56) References Cited

U.S. PATENT DOCUMENTS

| | | | |
|---|---|---|---|
| 4,873,392 A | 10/1989 | Le Van Mao | |
| 5,573,990 A * | 11/1996 | Wang ................ | B01J 29/40 502/65 |
| 2011/0124939 A1 * | 5/2011 | Minoux .............. | C07C 1/24 585/639 |
| 2011/0152479 A1 * | 6/2011 | Nesterenko ......... | B01J 21/08 526/75 |

FOREIGN PATENT DOCUMENTS

| | | |
|---|---|---|
| KR | 10-0891001 B1 | 3/2009 |
| KR | 10-2011-0043878 A | 4/2011 |
| KR | 10-1085046 B1 | 11/2011 |
| WO | 2012-174205 A1 | 12/2012 |
| WO | WO 2013/010662 A1 | 1/2013 |

OTHER PUBLICATIONS

Li et al., "Co-reaction of ethene and methanol over modified H-ZSM-5", Catalysis Communications 9, 2008, pp. 2515-2519.*
International Search Report for PCT/KR2014/003212 dated Jun. 27, 2014 from Korean Intellectual Property Office.
Hu, Yaochi et al., "Selective dehydration of bio-ethanol to ethylene catalyzed by lanthanum-phosphorous-modified ZASM-5: Influence of the fusel". Biotechnol. J., 2010, pp. 1186-1191, vol. 5.
Ramesh, Kanaparthi et al., "Synthesis, Characterization, and catalytic activity of phosphorus modified H-ZSM-5 catalysts in selective ethanol dehydration", Ind. Eng. Chem. Red., 2010, pp. 4080-4090, vol. 49.
Dongsheng Zhang et al., "Effect of P Content on the catalytic performance of P-modified HZSM-5 Catalysts in dehydration of Ethanol to ethylene.", Catalyst Letter, 2008, pp. 384-391 vol. 124.
Nina Zhan et al., "Lanthanum-Phosphorous modified HZSM-5 catalysts in dehydration of ethanol to ethylene: A comparative analysis", Catalysis Communications, 2010, pp. 633-637, vol. 11.
F.J. Machadoa et al., "The transformation of n-butane over Ga/SAPO-11, The role of extra framework gallium species", Applied Catalysis A: General, 2002, pp. 241-252, vol. 226.
R. Barthos et al., "Decomposition and Aromatization of Ethanol on ZSM-Based Catalysts", J. Phys. Chem B, 2006, pp. 21816-21825, vol. 110.
A. Ausavasukhi et al., "Additional Brønsted acid sites in [Ga]HZM-5 formed by the presence of water", Applied Catalysis A: General, 2009, pp. 93-98, vol. 361.
European Search Report for EP Application No. 14 785 350.1 dated Oct. 18, 2016 from European Patent Office.
Lidong Zhang et al., "Lanthanum Oxides-Improved Catalytic Performance of ZSM-5 in Toluene Alkylation with Methanol", Catalysis Letters, May 23, 2009, vol. 130, Issue 3, pp. 355-361.
Tabata et al., "Relationship between methane adsorption and selective catalytic reduction of nitrogen oxide by methane on gallium and indium ion-exchanged ZSM-5", Applied Catalysis B: Environmental, Aug. 12, 1995, vol. 6, Issue 3, pp. 225-236.
Denise Fan et al., "Ethylene Formation by Catalytic Dehydration of Ethanol with Industrial Considerations", Materials, Dec. 28, 2012, vol. 6, pp. 101-115.

* cited by examiner

*Primary Examiner* — Elizabeth D Wood
(74) *Attorney, Agent, or Firm* — Paratus Law Group, PLLC

(57) ABSTRACT

Provided are an ethanol dehydration catalyst having a high ethylene yield even at a low temperature region, as an ethanol dehydration catalyst for converting a feedstock including anhydrous ethanol or hydrous ethanol to ethylene, and a method of preparing ethylene by using the same. In the ethanol dehydration catalyst for converting a feedstock including anhydrous ethanol or hydrous ethanol to ethylene of the present invention, the catalyst includes 0.1 wt % to 0.5 wt % of lanthanum (La) or 0.05 wt % to 1 wt % of gallium (Ga) in ZSM-5.

1 Claim, 2 Drawing Sheets

ETHANOL DEHYDRATION CATALYST FOR ENERGY SAVING AND METHOD OF MANUFACTURING ETHYLENE USING SAME

CROSS REFERENCE TO PRIOR APPLICATION

This application is a National Stage Patent Application of PCT International Patent Application No. PCT/KR2014/003212 (filed on Apr. 14, 2014) under 35 U.S.C. § 371, which claims priority to Korean Patent Application No. 10-2013-0042846 (filed on Apr. 18, 2013) and 10-2014-0042722 (filed on Apr. 10, 2014), which are all hereby incorporated by reference in their entirety.

TECHNICAL FIELD

The present invention relates to an ethanol dehydration catalyst for energy saving and method of manufacturing ethylene using same, and more particularly, to an ethanol dehydration catalyst for converting a feedstock including anhydrous ethanol or hydrous ethanol to ethylene under a low temperature condition and a method of preparing ethylene by using the same.

The present invention is derived from a research project supported by the Industrial Strategic Technology Development Program of the Ministry of Trade, Industry and Energy in 2013 [2013-1004271, Development of New Innovative Chemical Process and New Catalyst].

BACKGROUND ART

Interests in renewable and sustainably producible new environmentally-friendly carbon resources have grown as the possibility of depletion of fossil fuels has increased. Among these resources, ethanol obtained through the fermentation of plants has been mass-produced in Brazil and the United States of America, and the ethanol has already been used as transportation energy in a number of developed countries and developing countries including the above countries.

Ethanol may not only be used as a possible alternative energy source, but may also be used in the preparation of various olefins including ethylene, as a basic raw material of petrochemical industry, through dehydration. A high-yield ethylene conversion reaction by the dehydration of ethanol is an endothermic reaction and the corresponding process may be regarded as an energy-intensive process in which a lot of heat is consumed for the pretreatment of raw materials and the removal of impurities in reactants and products. Thus, there is a need to design an energy-efficient catalytic process capable of producing ethylene in high yield at low temperature.

In general, alumina basic catalysts have been used as a commercially used catalyst for the dehydration of ethanol, and the production of ethylene is performed in a high temperature range of 300° C. to 500° C. This may require a lot of heat for the adjustment of reaction temperature and the preheating of raw materials and may cause a lot of costs and limitations due to high-temperature, high-pressure operation and design. Also, even if the production of ethylene in high yield is possible, in a case in which ethanol conversion rate and ethylene selectivity in a particular temperature region are not simultaneously secured by 98% or more, the performance of the catalyst may not only be degraded, but also additional costs due to a post-treatment purification process using ethylene as a raw material may be incurred and the purity of the product may be reduced.

Korean Patent No. 0891001 discloses a method of preparing a ZSM-5/SAPO-34 composite catalyst by mixing crystalline ZSM-5 obtained by hydrothermal synthesis in a preparation process of SAPO-34 and performing a series of processes of hydrothermal synthesis and sintering, and a method of preparing light olefin, which may maintain a selectivity of C2-C4 light olefin of 70 carbon mole % or more and a selectivity ratio [C3/C2] of propylene to ethylene of 1.0 or more by performing a reaction converting an oxygen-containing compound to light olefin in the presence of the ZSM-5/SAPO-34 composite catalyst obtained by the above method.

Korean Patent No. 1085046 relates to a method of preparing C2-C4 light olefins from an oxygen-containing compound, such as methanol and dimethyl ether, in the presence of a mordenite catalyst, wherein the patent discloses a method of preparing light olefin in which propylene and butene may be obtained in a yield of 60 wt % or more and, in particular, butene may be obtained in a high yield of about 30 wt %.

Korean Patent Application Laid-Open Publication No. 2011-0043878 discloses a method of preparing a microspherical SAPO-34 catalyst by preparing microspheres by spray drying a mixed slurry including a crystallized undried SAPO-34 slurry, a binder, and an additive, and then sintering the microspheres, and a catalyst having excellent reactivity as well as high strength, as a microspherical SAPO-34 catalyst for a circulating fluidized bed reactor which is prepared by the above method.

Non-Patent Document 1 (Dongsheng Zhang, Rijie Wang, Xiaoxia Yang, Effect of P Content on the catalytic performance of P-modified HZSM-5 Catalysts in dehydration of Ethanol to ethylene, Catalyst Letter 124, 384-391 (2008)) is a paper related to dehydration effect of a P-modified H-ZSM-5 zeolite catalyst in which a H-ZSM-5 catalyst is impregnated with phosphorus (P), wherein experiments on the conversion of ethanol to ethylene using the P-modified H-ZSM-5 catalyst at various temperatures have been conducted. In this paper, since ethylene is mainly produced at 573 K to 713 K with respect to a catalyst having a phosphorous content of 3.4 wt % or more and ethylene and high hydrocarbons (C3-C9+aliphatic and aromatic) are produced at high temperature with respect to a catalyst having a phosphorous content of 3.4 wt % or less, it may be understood that high-temperature dehydration of the catalyst is an essential reaction to enable the conversion of ethanol to ethylene in the presence of the catalyst having a phosphorous content of 3.4 wt % or more.

With respect to the catalysts disclosed in these patents and non-patent document, the yield of ethylene is relatively low, there is a limitation in that high-purity ethylene is not selectively produced, and it may be referred to as an inefficient process in which high energy is consumed for the high-temperature reaction.

U.S. Pat. No. 4,873,392 discloses a catalyst for conversion of ethanol to ethylene, as a lanthanum-modified H-ZSM-catalyst, in which catalytic activity at low temperature is improved. In the patent, although the possibility of the activity of the ethanol dehydration catalyst in a relatively low-temperature region has been suggested, there is a limitation in that very low space velocity (weight hourly space velocity (WHSV)) is required to exhibit significant catalytic activity and the yield of ethylene is also not satisfactory.

Non-Patent Document 2 (Nina Zhan, Yi Hu, Heng Li, Dinghua Yu, Yuwang Han, He Huang, Lanthanum-Phosphorous modified HZSM-5 catalysts in dehydration of ethanol to ethylene: A comparative analysis, Catalysis Communications 11, 633-637 (2010)) is a paper related to a method of preparing ethylene from hydrous ethanol using a ZSM-5 catalyst in which lanthanum and phosphorous are simultaneously impregnated, wherein the catalyst, in which lanthanum and phosphorous are simultaneously impregnated, has an effect of preventing the loss of alumina in a ZSM-5 catalyst skeleton according to the supply of a raw material having a high water content, but the activity may be reduced when a raw material having a high ethanol content is used and the reaction temperature may be set to a high temperature in order to address this issue.

Some prior art documents suggest examples of using catalysts in which gallium is introduced into zeolite.

In Non-Patent Document 3 (F. J. Machadoa, C. M. Lopez, Y. Camposa, A. Bolivar, S. Yunes, The transformation of n-butane over Ga/SAPO-11, The role of extra-framework gallium species, Applied Catalysis A: General, 226, 241-252 (2002)), a zeolite catalyst having gallium introduced thereinto, as a dehydrogenation catalyst required for the preparation of isobutene from normal butane, was used in the preparation of olefin. In this paper, it is reported that when the zeolite catalyst, to which gallium was added, was used as a catalyst under atmospheric pressure and relatively high temperature reaction condition, i.e., 500° C., the selectivity of isobutene among products was improved through the dehydrogenation of normal butane. Specifically, the used catalysts included SAPO-11, as a starting catalyst, and a catalyst in which gallium was introduced in an amount of 0.25 wt % to 2.2 wt %. However, since an olefin compound was prepared by using a hydrocarbon compound, instead of alcohol, as a raw material, it is reported that the reaction followed a mechanism (reaction mechanism) of dehydrogenation instead of dehydration and the selectivity of olefin was improved at a high temperature of 500° C.

In Non-Patent Document 4 (R. Barthos, A. Szechenyi, and F. Solymosi/Decomposition and Aromatization of Ethanol on ZSM-Based Catalysts/J. Phys. Chem. B/110, 21816-21825 (2006)), research into the characteristics of a catalyst related to the improvement of the selectivity of an aromatic compound was conducted by using a raw material to which ethanol or ethylene was added. Although the research resulted in screening a catalyst having excellent selectivity in the preparation of the aromatic compound at a high temperature of 500° C. to 600° C. among catalysts prepared by using H-ZSM5 as a starting catalyst and adding a metal (molybdenum, rhenium, zinc, gallium, etc.) in an amount of 2 wt %, research into the improvement of the selectivity and yield of ethylene obtained as a final product from the dehydration of ethanol was not conducted.

Non-Patent Document 5 (A. Ausavasukhi, T. Sooknoi/Additional Brønsted acid sites in [Ga]HZSM-5 formed by the presence of water/Applied Catalysis A: General/361, 93-98 (2009)) also reports research results similar to those of Non-Patent Document 2. However, experimental results suggested that the yield of aromatic compound was improved when a catalyst hydrothermally treated with 1 wt % of steam at 425° C. was used or water was directly added to a reactant stream in the preparation of Ga-ZSM-5 by adding 3 wt % of gallium.

With respect to these non-patent documents, since alcohols were not used as a reactant or ethylene was not a desired reaction product, it may be considered that these documents are significantly different from the scope of the present invention to be later described, i.e., an efficient catalytic reaction usable in the preparation of ethylene through the dehydration of ethanol, in terms of technical objectives as well as a chemical route. The catalysts prepared according to the methods suggested in these documents may be ineffective or may have very limited selectivity or yield of ethylene when ethylene is prepared through the dehydration of ethanol.

DISCLOSURE OF THE INVENTION

Technical Problem

The present invention provides an ethanol dehydration catalyst having a high ethylene yield even at a low temperature region, as an ethanol dehydration catalyst for converting a feedstock including anhydrous ethanol or hydrous ethanol to ethylene, and a method of preparing ethylene by using the same.

The present invention also provides an ethanol dehydration catalyst which has improved thermal stability and good effect of preventing deactivation due to coking, and a method of preparing ethylene by using the same.

The present invention also provides an ethanol dehydration catalyst which may allow ethylene to be obtained in high yield without deactivation for a long time even in a low temperature region and under a reaction condition of a relatively high space velocity, and a method of preparing ethylene by using the same.

Technical Solution

According to a first aspect of the present invention, there is provided an ethanol dehydration catalyst for converting a feedstock including anhydrous ethanol or hydrous ethanol to ethylene, wherein the catalyst includes 0.1 wt % to 0.5 wt % of lanthanum (La) in ZSM-5.

Also, the catalyst may further include 0.01 wt % to 1 wt % of phosphorous (P).

According to a second aspect of the present invention, there is provided an ethanol dehydration catalyst for converting a feedstock including anhydrous ethanol or hydrous ethanol to ethylene, wherein the catalyst includes 0.05 wt % to 1 wt % of gallium (Ga) in ZSM-5.

Also, the catalyst may further include 0.05 wt % to 0.5 wt % of La.

The hydrous ethanol may have a water content of 30 wt % or less.

The ZSM-5 may have a $Si/Al_2$ molar ratio of 20 to 45.

The catalyst according to the first aspect of the present invention may have an ethanol conversion rate of 98% or more and an ethylene selectivity of 98% or more which are measured under a condition:

[Measurement Condition]

the ethanol conversion rate and the ethylene selectivity are measured after dehydration at a space velocity (WHSV) of 5 $hr^{-1}$ and a temperature of 240° C. for 240 hours.

The catalyst according to the second aspect of the present invention may have an ethanol conversion rate of 99% or more and an ethylene selectivity of 96% or more which are measured under a condition:

[Measurement Condition]

the ethanol conversion rate and the ethylene selectivity are measured after dehydration at a space velocity (WHSV) of 5 $hr^{-1}$ and a temperature of 240° C. for 240 hours.

According to another aspect of the present invention, there is provided a method of preparing ethylene by dehydrating a feedstock including anhydrous ethanol or hydrous ethanol, wherein the feedstock is reacted at a space velocity (WHSV) of 0.1 h$^{-1}$ to 50 h$^{-1}$ and a temperature of 220° C. to 250° C. in the presence of the ethanol dehydration catalyst according to the first aspect of the present invention.

According to another aspect of the present invention, there is provided a method of preparing ethylene by dehydrating a feedstock including anhydrous ethanol or hydrous ethanol, wherein the feedstock is reacted at a space velocity (WHSV) of 0.1 h$^{-1}$ to 50 h$^{-1}$ and a temperature of 220° C. to 260° C. in the presence of the ethanol dehydration catalyst according to the second aspect of the present invention.

Advantageous Effects

The performance of a non-homogeneous catalyst for preparing ethylene by dehydration of ethanol may be exemplified in terms of high yield, which may secure high ethanol conversion rate and high ethylene selectivity, and long lifetime which enables stable operation of a catalytic process while maintaining the activity of the catalyst for a long time. For this purpose, there is a need to design an optimum catalyst which may maximize the yield of ethylene, as a desired reaction, and may suppress the speed of deactivation caused by carbon deposition on the surface of the catalyst and in pores due to coking as a side reaction. In particular, in a case in which high-purity production of ethylene used for the preparation of ethylene glycol in petrochemical processes is not performed, the lifetime of a catalyst for a partial oxidation process producing ethylene oxide may be reduced, and large energy consumption is necessary for a post-purification process which is required therefor.

According to the present invention, provided are an energy-saving ethanol dehydration catalyst, as an ethanol dehydration catalyst for converting a feedstock including anhydrous ethanol or hydrous ethanol to ethylene, which may not only prepare ethylene in high yield by significantly suppressing coking, as a side reaction, even in a low temperature range of 220° C. to 260° C. for lanthanum and 220° C. to 260° C. for gallium by using ZSM-5 as a basic catalyst and including lanthanum or gallium in an optimum amount, but may also allow ethylene to be obtained in high yield without deactivation for a long time even under a reaction condition of a relatively high space velocity, and a method of preparing ethylene by using the same.

MODE FOR CARRYING OUT THE INVENTION

Figure 1:
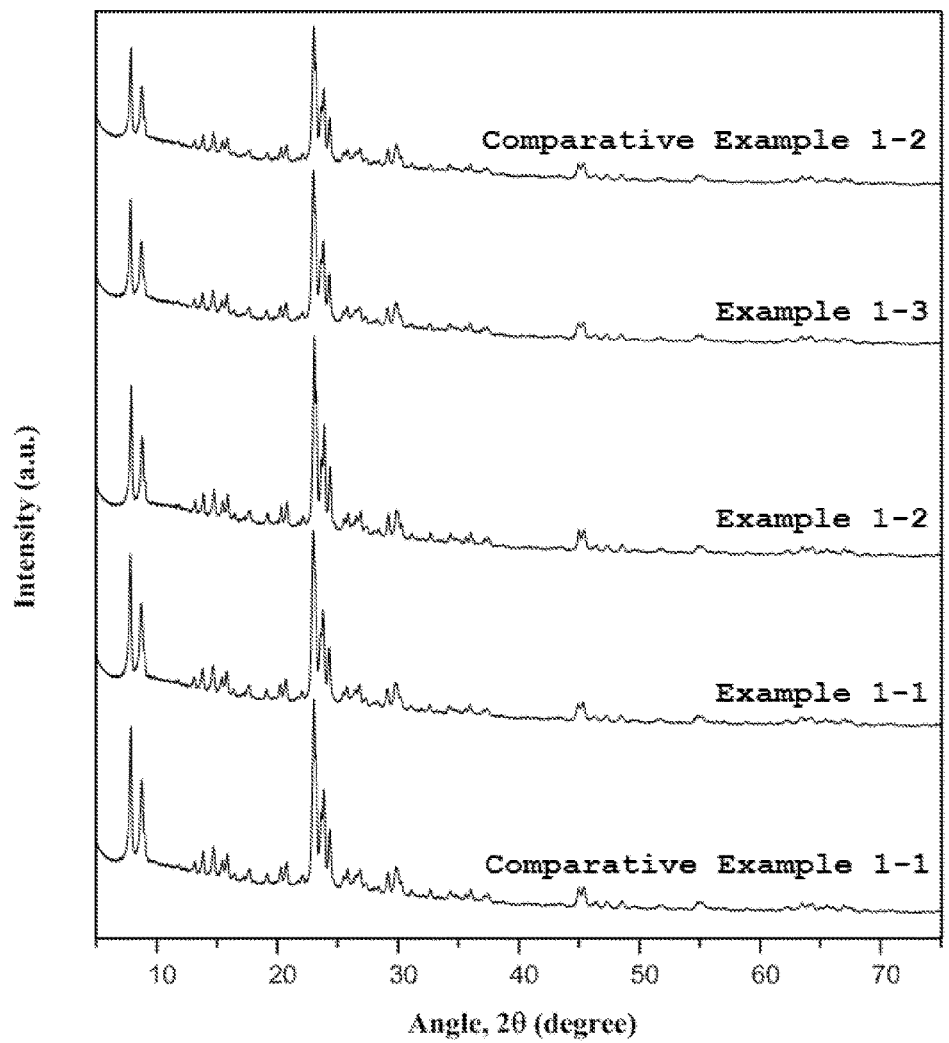
FIG. 1 is a graph illustrating results of X-ray diffraction analysis of ethanol dehydration catalysts prepared according to Examples 1-1 to 1-3 and Comparative Examples 1-1 and 1-2 of the present invention.

Hereinafter, the present invention will be described in detail, according to specific examples. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention. Accordingly, since the embodiments set forth in the present specification and the configurations illustrated in the drawings are shown by way of example and do not represent all the technological spirit of the present invention, it should be understood that embodiments of the present invention are capable of various modifications, equivalents, and alternatives at the time of present application.

In an ethanol dehydration catalyst for converting a feedstock including anhydrous ethanol or hydrous ethanol to ethylene, in order to selectively prepare ethylene in high yield while increasing or maintaining dehydration performance of the catalyst in a low-temperature region, it is important to increase conversion rate and selectivity of the desired product by optimizing the selection of a basic catalyst, the selection of appropriate additives and composition, and supply conditions of reactants. Accordingly, there is a need to develop a catalyst for designing an energy-saving process capable of obtaining ethylene in high yield, and there is also a need to develop a catalyst capable of maintaining its activity for a long time in order to secure economic efficiency associated with stable operation and maintenance of the process. In this situation, as a result of a significant amount of research, the present inventors found that there is an optimal amount of lanthanum or gallium in which ethylene may not only be prepared in high yield by significantly suppressing coking in a low-temperature region by selecting highly acidic ZSM-5 having a specific Si/Al$_2$ molar ratio as a basic catalyst and including lanthanum or gallium as a specific metallic component, but ethylene may also be obtained in high yield without deactivation for a long time under a reaction condition of a high space velocity, thereby leading to the completion of the present invention.

Thus, according to a first aspect of the present invention, disclosed is an ethanol dehydration catalyst for converting a feedstock including anhydrous ethanol or hydrous ethanol to ethylene, wherein the catalyst includes 0.1 wt % to 0.5 wt % of lanthanum (La) in ZSM-5.

Also, according to a second aspect of the present invention, disclosed is an ethanol dehydration catalyst for converting a feedstock including anhydrous ethanol or hydrous ethanol to ethylene, wherein the catalyst includes 0.05 wt % to 1 wt % of gallium (Ga) in ZSM-5.

In the present invention, the feedstock includes anhydrous ethanol or hydrous ethanol, and is a raw material in which an oxygen-containing compound is substantially composed of ethanol. Compositions of the anhydrous ethanol and hydrous ethanol are not particularly limited, but the anhydrous ethanol, for example, may be 99.96 wt % of synthetic ethanol, and the hydrous ethanol may have a water content of 30 wt % or less, and, for example, may be 95 wt % of ethanol derived from carbohydrate-based, wood-based, and starch-based plants. In a case in which the water content of the hydrous ethanol is greater than 30 wt %, since a dealumination phenomenon of the catalyst may be accelerated, the hydrous ethanol may not be suitable for a raw material. Also, a trace of hydrocarbon-based impurities (alcohols or aldehydes having different number of carbon atoms), which may be included in an amount of about a few tens to a few hundreds of ppm in the feedstock, may be removed through a purification process before and after the reaction process and it may be considered that the hydrocarbon-based impurities do not significantly affect the preparation of ethylene.

With respect to the ethanol dehydration catalyst in the present invention, ZSM-5, as a highly acidic, non-homogeneous acid catalyst, is selected as a basic catalyst in order to increase the activity of the catalyst which is required for the dehydration. The ZSM-5 may be used after being converted to H-ZSM-5 having hydrogen ions as a cation according to a method known in the art. For example, in a case in which the cation of the ZSM-5 basic catalyst is not a hydrogen ion, the ZSM-5 may be prepared by sintering at a temperature of 450° C. to 550° C. for 6 hours or more after ion exchange. With respect to acidity of the basic catalyst, the density of Brønsted acid sites may be adjusted through dealumination and, for this purpose, a base support required for the preparation may be subjected to a steam treatment at a temperature of 500° C. to 700° C.

After the conversion to the H-ZSM-5, the lanthanum or gallium, as the metallic component, may be introduced by using a lanthanum precursor compound or gallium precursor compound in such a manner that lanthanum or gallium is impregnated so as for the lanthanum precursor compound or gallium precursor compound having a desired composition to be dispersed over a large area in the pores of the catalyst and the impregnation is completed by sintering. An ion exchange method or impregnation method may be used as a method of introducing lanthanum or gallium, but the impregnation method facilitating the control of the acidity, particularly, the desired composition, may be used. A method of impregnating H-ZSM-5 with a lanthanum or gallium precursor, for example, may be performed by hydrating a lanthanum precursor or gallium precursor in water, impregnating H-ZSM-5 by adding the prepared H-ZSM-5 to the hydrated solution, removing a solvent at a temperature of 70° C. to 90° C., drying at a temperature of 100° C. to 200° C. for 6 hours to 24 hours, and sintering at a temperature of 450° C. to 550° C. for 6 hours or more. In a case in which the sintering temperature is excessively low, for example, less than 450° C., since the metal is not normally added due to the non-decomposition of the precursor material, the activity of the catalyst may be reduced. In a case in which the sintering temperature is excessively high, for example, greater than 550° C., since acid characteristics and structure of the prepared catalyst are changed, the desired activity of the catalyst may be difficult to be obtained.

In this case, it is important to set an amount of the introduced lanthanum or gallium in an optimum range in consideration of effects on the surface area, strong acidity, and cation structure distribution of the finally prepared ethanol dehydration catalyst, and activity in a low-temperature region, ethanol conversion rate and ethylene selectivity, carbon deposition amount, or prolonged activity maintenance during dehydration.

Thus, as the amount of the introduced lanthanum to dramatically improve both the above-described characteristics and activity of the catalyst in the present invention, it was confirmed that an optimum effect may be achieved in a range of 0.1 wt % to 0.5 wt %, particularly, 0.2 wt % to 0.4 wt %, and, more particularly, 0.2 wt % to 0.3 wt %, of lanthanum based on a weight of the finally prepared catalyst. Also, as the amount of the introduced gallium, it was confirmed that an optimum effect may be achieved in a range of 0.05 wt % to 1 wt %, particularly, 0.1 wt % to 0.75 wt %, and, more particularly, 0.25 wt % to 0.5 wt %, of gallium based on the weight of the finally prepared catalyst.

In a case in which the amount of the lanthanum is less than 0.1 wt % or greater than 0.5 wt %, the yield in a low-temperature reaction region may not be satisfactory, the carbon deposition amount may increase, and the prolonged activity maintenance may be difficult. Also, in a case in which the amount of the gallium is less than 0.05 wt % or greater than 1 wt %, the yield in a low-temperature reaction region may not be satisfactory, the carbon deposition amount may increase, and the prolonged activity maintenance may be difficult.

For example, lanthanum chloride ($LaCl_3$), lanthanum oxide ($La_2O_3$), and anhydrous or hydrous lanthanum nitrate ($La(NO_3)_3$).$nH_2O$; n≥0) may be used as the lanthanum precursor, and the lanthanum precursor may be quantified and added to match the desired final content of the lanthanum during the impregnation of ZSM-5.

Also, for example, gallium (II) chloride ($Ga_2Cl_4$), gallium (III) chloride ($GaCl_3$), gallium oxide ($Ga_2O_3$), and anhydrous or hydrous gallium (III) nitrate ($Ga(NO_3)_3$).$nH_2O$; n≥0) may be used as the gallium precursor, and the gallium precursor may be quantified and added to match the desired final content of the gallium during the impregnation of ZSM-5.

In the present invention, it is desirable to select a catalyst having a relatively low $Si/Al_2$ molar ratio as the ZSM-5 used as the basic catalyst. The reason for this is that when the alumina content is low, i.e., the $Si/Al_2$ molar ratio is high, faster deactivation is performed in a wide temperature range of 200° C. to 300° C. Also, although the introduced lanthanum or gallium does not decrease the density of silica, the lanthanum or gallium may decrease the density of alumina to significantly limit the promotion of the activity. Such changes in the characteristics of the catalyst according to the introduction of lanthanum or gallium may be confirmed by the fact that the ratio of silica is not significantly changed, but the ratio of alumina is significantly changed during elemental analysis, such as X-ray fluorescence (XRF) spectrometry, after the preparation of the catalyst. Thus, in the present invention, it is desirable to select ZSM-5 with a high density of alumina, and since the introduced material may be uniformly dispersed and the limitation in activity may be reduced when ZSM-5 having a $Si/Al_2$ molar ratio of 20 to 50, for example, 23 to 35, is used in consideration of the amount of the introduced lanthanum or gallium, the ZSM-5 is suitable for the support. In a case in which the $Si/Al_2$ molar ratio is less than 20, there may be a concern of deactivation due to coking while the acidity of the catalyst is increased, and in a case in which the $Si/Al_2$ molar ratio is greater than 45, the ethanol conversion rate may be reduced because the acid characteristics of the catalyst are not satisfactory.

In the ethanol dehydration catalyst having lanthanum introduced thereto according to the first aspect of the present invention, phosphorus (P) may be further included in the ZSM-5. The introduction of the phosphorus may favorably affect the improvement in the thermal stability and the suppression of the deactivation of the catalyst due to coking as well as the changes in fundamental reactive properties of the catalyst. However, it is not effective in maintaining the same activity as the basic catalyst in a low-temperature region even if it is added in a slightly excessive amount. Thus, in the present invention, the phosphorus may be added in an amount of 1 wt % or less based on the weight of the finally prepared catalyst.

The introduction of the phosphorus may be performed by a method similar to that used in the introduction of the lanthanum, i.e., a method of hydrating a phosphorus precursor in water, adding ZSM-5 having lanthanum introduced thereto to the hydrated solution, and drying and sintering the resultant product. In this case, the introduction of the phosphorus may also be performed by changing the order of the introduction of lanthanum and phosphorous, i.e., a method in which phosphorous is first introduced and lanthanum is then introduced into ZSM-5 having phosphorous introduced thereinto. However, in a case in which lanthanum and phosphorous are simultaneously added instead of being sequentially introduced, it is not desirable because salt precipitation may occur due to the ion exchange of the heterogeneous precursor mixture or desired elements may not be uniformly introduced due to limited mass transfer. Herein, when using an ion exchange method, the order of the introduction of the desired elements may be determined by the relative degree of ionization, and when using an impregnation method, the method is performed by dissolving the precursor in a solvent, but it is desirable to allow an inner surface of the catalyst to be impregnated with a large amount of the precursor.

As the phosphorous precursor, for example, phosphoric acid ($H_3PO_4$), ammonium phosphate (($NH_4$)$H_2PO_4$), diammonium phosphate (($NH_4$)$_2HPO_4$), and ammonium polyphosphate (($NH_4$)$_4P_2O_7$) may be used alone or in a mixture thereof, and the phosphorous precursor may be quantified and added to match the desired final content of the phosphorous during the addition to the ZSM-5.

Also, the ethanol dehydration catalyst having gallium introduced thereinto according to the second aspect of the present invention may be prepared by using ZSM-5, which is modified by adding a heterogeneous metal effective in the dehydration, as a starting catalyst. For example, the reactivity of the catalyst may be slightly improved by introducing gallium into the ZSM-5 having lanthanum added thereto at an optimal composition, and it may have a favorable effect in maintaining long-term performance. However, in a case in which a total amount of the metal added is greater than 1 wt %, it may not be effective in increasing the activity of the catalyst and maintaining the stability. Thus, in the present invention, lanthanum is added such that the total amount of the metal added is not greater than 1 wt % based on the weight of the finally prepared catalyst, and the lanthanum may be added in an amount of 0.05 wt % to 0.5 wt % in consideration of the desired amount of gallium.

The introduction of the lanthanum into the ethanol dehydration catalyst having gallium introduced thereinto according to the second aspect of the present invention may be performed by a method similar to that used in the introduction of the gallium, i.e., a method of hydrating a gallium precursor in water, adding ZSM-5 having lanthanum introduced thereinto to the hydrated solution, and drying and sintering the resultant product. In this case, the introduction of the lanthanum may also be performed by changing the order of the introduction of lanthanum and gallium, i.e., a method in which gallium is first introduced and lanthanum is then introduced into ZSM-5 having gallium introduced thereinto. However, in a case in which lanthanum and gallium are simultaneously added instead of being sequentially introduced, it is not desirable because salt precipitation may occur due to the ion exchange of the heterogeneous precursor mixture or desired elements may not be uniformly introduced due to limited mass transfer. Herein, when using an ion exchange method, the order of the introduction of the desired elements may be determined by the relative degree of ionization, and when using an impregnation method, the method is performed by dissolving the precursor in a solvent, but it is desirable to allow an inner surface of the catalyst to be impregnated with a large amount of the precursor.

As the lanthanum precursor, for example, lanthanum chloride ($LaCl_3$), lanthanum oxide ($La_2O_3$), and anhydrous or hydrous lanthanum nitrate ($La(NO_3)_3$).$nH_2O$; n≥0) may be used alone or in a mixture thereof, and the lanthanum precursor may be quantified and added to match the desired final content of the lanthanum during the addition to the ZSM-5.

The above-described ethanol dehydration catalyst according to the present invention is a catalyst, in which lanthanum metal or phosphorous, as a non-metallic component, with the lanthanum metal is added in an amount in the optimal range so as to be dispersed in a highly acidic ZSM-5 support, or a catalyst in which gallium or lanthanum with the gallium is added in an amount in the optimal range so as to be dispersed in a highly acidic ZSM-5 support, wherein since reactant conversion rate and ethylene selectivity may be improved when the reaction is performed under specific reaction conditions, particularly, in a low-temperature region, as confirmed in the following examples and experimental examples and the addition of the metallic component having a specific composition may have an excellent effect of increasing the activity of the catalyst and maintaining the performance of the catalyst, the ethanol dehydration catalyst according to the present invention may address limitations faced during the preparation of ethylene by a typical ethanol dehydration process, such as use of high temperature energy, low conversion rate and selectivity, and the reduction of the catalytic activity within a short period of time.

For example, the ethanol dehydration catalyst according to the first aspect of the present invention may have a carbon deposition amount, which is measured by thermogravimetric analysis (TGA) after dehydration at 240° C. for 11.5 hours, of less than 1 wt %, and an ethanol conversion rate of 98% or more and an ethylene selectivity of 98% or more which are measured after dehydration at a space velocity (weight hourly space velocity (WHSV)) of 5 $hr^{-1}$ and 240° C. for 240 hours.

Also, the ethanol dehydration catalyst according to the second aspect of the present invention may have a carbon deposition amount, which is measured by TGA after dehydration at 240° C. for 11.5 hours, of less than 1 wt %, and an ethanol conversion rate of 99% or more and an ethylene selectivity of 96% or more which are measured after dehydration at a space velocity (WHSV) of 5 $hr^{-1}$ and 240° C. for 240 hours.

The ethanol dehydration catalyst according to the present invention may be used in a method of preparing ethylene by dehydrating a feedstock including anhydrous ethanol or hydrous ethanol, may prepare ethylene by reacting the feedstock under conditions including a reaction temperature of 220° C. to 250° C. and a space velocity (WHSV) of 0.1 $hr^{-1}$ to 50 $hr^{-1}$ in the presence of the above-described ethanol dehydration catalyst according to the first aspect of the present invention, and may prepare ethylene by reacting the feedstock under conditions including a reaction temperature of 220° C. to 260° C. and a space velocity (WHSV) of 0.1 $hr^{-1}$ to 50 $hr^{-1}$ in the presence of the ethanol dehydration catalyst according to the second aspect of the present invention.

The anhydrous ethanol or hydrous ethanol usable as the feedstock is as described above, and the feedstock may be provided in an evaporated form through preheating to minimize large changes in the reaction temperature due to latent heat. In this case, nitrogen gas or the like may be used as an inert carrier and may be used within a range that does not affect the performance of the catalyst, specifically, under the reaction condition in which a volume ratio of the evaporated ethanol feedstock to the inert carrier is 100 or less. In a case in which the volume ratio is greater than 100, it may be out of the range of mass transfer in which the reactants arrive at the surface of the catalyst.

When the ethanol dehydration catalyst according to the present invention is used in the dehydration, the reaction temperature may be in a range of 200° C. to 300° C., but the catalyst according to the first aspect of the present invention may be used in a temperature range of 220° C. to 250° C. and the catalyst according to the second aspect of the present invention may be used in a temperature range of 220° C. to 260° C. In a case in which the reaction temperature is less than 220° C., the production of diethylene ether (DEE) may thermodynamically be a dominant side reaction and the conversion rate may also be significantly reduced. In a case in which the reaction temperature is greater than 250° C. in the first aspect of the present invention or 260° C. in the second aspect of the present invention, the conversion rate may be close to 100%, but it may not be suitable for the preparation of ethylene because heavy hydrocarbons including an aromatic compound are produced.

The space velocity (WHSV) may be in a range of 0.1 hr$^{-1}$ to 50 hr$^{-1}$, for example, 0.5 hr$^{-1}$ to 10 hr$^{-1}$. The space velocity denotes a net mass flow rate of ethanol in the raw material with respect to a mass of the catalyst added in the reaction, wherein the space velocity may be measured through the control of an initial mass of the catalyst and a supply flow of the ethanol. In a case in which the space velocity is less than 0.1 hr$^{-1}$, the conversion rate may be increased, but mass production of ethylene may be difficult, and in a case in which the space velocity is greater than 50 hr$^{-1}$, the conversion rate may be reduced and the deactivation of the catalyst and the reduction of the lifetime of the catalyst may occur.

Example 1-1

15 g of H-ZSM-5 (CBV 3024E, Zeolyst International, USA) having a Si/Al$_2$ molar ratio of 30 was mixed with lanthanum nitrate hexahydrate (La(NO$_3$)$_3$.6H$_2$O) (99.99% trace metal basis, product No. 331937, Sigma-Aldrich Co. LLC., USA) which was quantified such that a lanthanum content corresponded to 0.1 wt % based on a weight of a finally prepared catalyst and was prepared in an aqueous solution. In this case, water was added by measuring an amount of the water which may be absorbed in pores of the catalyst. Thereafter, the mixture was mixed for 20 minutes to 60 minutes and dried for 12 hours in an oven maintained at 80° C. Thereafter, a dried solid was ground. Using temperature programming, the ground solid was dried at 200° C. for about 1 hour and sintered in a sintering furnace for 6 hours, after the temperature was increased to 550° C., to prepare an ethanol dehydration catalyst.

Example 1-2

An ethanol dehydration catalyst was prepared in the same manner as in Example 1-1 except that lanthanum nitrate hexahydrate was quantified such that the lanthanum content corresponded to 0.25 wt % in Example 1-1.

Example 1-3

An ethanol dehydration catalyst was prepared in the same manner as in Example 1-1 except that lanthanum nitrate hexahydrate was quantified such that the lanthanum content corresponded to 0.5 wt % in Example 1-1.

Example 1-4

15 g of H-ZSM-5 having a Si/Al$_2$ molar ratio of 30 was mixed with phosphoric acid (85%, product No. 452289, Sigma-Aldrich Co. LLC., USA) which was quantified such that a phosphor content corresponded to 0.5 wt % based on a weight of a finally prepared catalyst and was prepared in an aqueous solution. In this case, water was added by measuring an amount of the water which may be absorbed in pores of the catalyst. Thereafter, the mixture was mixed for 20 minutes to 60 minutes and dried for 12 hours in an oven maintained at 80° C. Thereafter, a dried solid was ground. Using temperature programming, the ground solid was dried at 200° C. for about 1 hour and sintered in a sintering furnace for 6 hours, after the temperature was increased to 550° C., to prepare a catalyst into which phosphorus was introduced. Thereafter, the catalyst into which phosphorus was introduced was mixed with lanthanum nitrate hexahydrate which was quantified such that a lanthanum content corresponded to 0.5 wt % based on the weight of the finally prepared catalyst and was prepared in an aqueous solution. Then, the method described in Example 1-1 was repeated to prepare an ethanol dehydration catalyst into which phosphorus and lanthanum were introduced.

Example 1-5

An ethanol dehydration catalyst was prepared in the same manner as in Example 1-4 except that phosphoric acid was quantified such that the phosphorus content corresponded to 1 wt % in Example 1-4.

Example 1-6

An ethanol dehydration catalyst was prepared in the same manner as in Example 1-2 except that H-ZSM-5 (CBV 2314, Zeolyst International, USA) having a Si/Al$_2$ molar ratio of 23 was used in Example 1-2.

Comparative Example 1-1

H-ZSM-5 having a Si/Al$_2$ molar ratio of 30 was prepared as an ethanol dehydration catalyst.

Comparative Example 1-2

An ethanol dehydration catalyst was prepared in the same manner as in Example 1-1 except that lanthanum nitrate hexahydrate was quantified such that the lanthanum content corresponded to 1 wt % in Example 1-1.

Comparative Example 1-3

An ethanol dehydration catalyst was prepared in the same manner as in Example 1-1 except that lanthanum nitrate hexahydrate was quantified such that the lanthanum content corresponded to 2 wt % in Example 1-1.

Comparative Example 1-4

15 g of H-ZSM-5 having a Si/Al$_2$ molar ratio of 30 was mixed with an 85% phosphoric acid aqueous solution which was prepared and quantified such that a phosphor content corresponded to 2 wt % based on a weight of a finally prepared catalyst. In this case, water was added by measuring an amount of the water which may be absorbed in pores of the catalyst. Thereafter, the mixture was mixed for 20 minutes to 60 minutes and dried for 12 hours in an oven maintained at 80° C. Thereafter, a dried solid was ground. Using temperature programming, the ground solid was dried at 200° C. for about 1 hour and sintered in a sintering furnace for 6 hours, after the temperature was increased to 550° C., to prepare a catalyst into which phosphorus was introduced.

Comparative Example 1-5

An ethanol dehydration catalyst was prepared in the same manner as in Example 1-4 except that phosphoric acid was quantified such that the phosphorus content corresponded to 2 wt % in Example 1-4.

Comparative Example 1-6

An ethanol dehydration catalyst was prepared in the same manner as in Example 1-2 except that H-ZSM-5 (CBV 5524G, Zeolyst International, USA) having a $Si/Al_2$ molar ratio of 50 was used in Example 1-2.

Comparative Example 1-7

An ethanol dehydration catalyst was prepared in the same manner as in Example 1-2 except that H-ZSM-5 (CBV 8014, Zeolyst International, USA) having a $Si/Al_2$ molar ratio of 80 was used in Example 1-2.

Example 2-1 g of H-ZSM-5 (CBV 3024E, Zeolyst International, USA) having a $Si/Al_2$ molar ratio of 30 was mixed with gallium nitrate hydrate $(Ga(NO_3)_3 \cdot xH_2O)$ (99.99% trace metal basis, product No. 289892, Sigma-Aldrich Co. LLC., USA) which was quantified such that a gallium content corresponded to 0.05 wt % based on a weight of a finally prepared catalyst and was prepared in an aqueous solution. In this case, water was added by measuring an amount of the water which may be absorbed in pores of the catalyst. Thereafter, the mixture was mixed for 20 minutes to 60 minutes and dried for 12 hours in an oven maintained at 80° C. Thereafter, a dried solid was ground. Using temperature programming, the ground solid was dried at 200° C. for about 1 hour and sintered in a sintering furnace for 6 hours, after the temperature was increased to 550° C., to prepare an ethanol dehydration catalyst.

Example 2-2

An ethanol dehydration catalyst was prepared in the same manner as in Example 2-1 except that gallium nitrate hydrate was quantified such that the gallium content corresponded to 0.1 wt % in Example 2-1.

Example 2-3

An ethanol dehydration catalyst was prepared in the same manner as in Example 2-1 except that gallium nitrate hydrate was quantified such that the gallium content corresponded to 0.25 wt % in Example 2-1.

Example 2-4

An ethanol dehydration catalyst was prepared in the same manner as in Example 2-1 except that gallium nitrate hydrate was quantified such that the gallium content corresponded to 0.5 wt % in Example 2-1.

Example 2-5

An ethanol dehydration catalyst was prepared in the same manner as in Example 2-1 except that gallium nitrate hydrate was quantified such that the gallium content corresponded to 0.75 wt % in Example 2-1.

Example 2-6

An ethanol dehydration catalyst was prepared in the same manner as in Example 2-1 except that gallium nitrate hydrate was quantified such that the gallium content corresponded to 1 wt % in Example 2-1.

Example 2-7

The catalyst having a lanthanum content of 0.25 wt % prepared in Example 1-2 was mixed with gallium nitrate hydrate which was quantified such that a gallium content corresponded to 0.25 wt % based on a weight of a finally prepared catalyst and was prepared in an aqueous solution. Then, the method described in Example 2-1 was repeated to prepare an ethanol dehydration catalyst into which lanthanum and gallium were introduced.

Example 2-8

An ethanol dehydration catalyst was prepared in the same manner as in Example 2-7 except that gallium nitrate hydrate was quantified such that the gallium content corresponded to 0.5 wt % in Example 2-7.

Example 2-9

An ethanol dehydration catalyst was prepared in the same manner as in Example 2-3 except that H-ZSM-5 (CBV 2314, Zeolyst International, USA) having a $Si/Al_2$ molar ratio of 23 was used in Example 2-3.

Comparative Example 2-1

An ethanol dehydration catalyst was prepared in the same manner as in Example 2-1 except that gallium nitrate hydrate was quantified such that the gallium content corresponded to 0.02 wt % in Example 2-1.

Comparative Example 2-2

An ethanol dehydration catalyst was prepared in the same manner as in Example 2-1 except that gallium nitrate hydrate was quantified such that the gallium content corresponded to 1.25 wt % in Example 2-1.

Comparative Example 2-3

An ethanol dehydration catalyst was prepared in the same manner as in Example 2-7 except that gallium nitrate hydrate was quantified such that the gallium content corresponded to 0.75 wt % in Example 2-7.

Comparative Example 2-4

An ethanol dehydration catalyst was prepared in the same manner as in Example 2-7 except that lanthanum nitrate hexahydrate was quantified such that the lanthanum content corresponded to 0.75 wt % and gallium nitrate hydrate was quantified such that the gallium content corresponded to 0.25 wt % in Example 2-7.

Comparative Example 2-5

An ethanol dehydration catalyst was prepared in the same manner as in Example 2-3 except that H-ZSM-5 (CBV 5524G, Zeolyst International, USA) having a Si/Al$_2$ molar ratio of 50 was used in Example 2-3.

Comparative Example 2-6

An ethanol dehydration catalyst was prepared in the same manner as in Example 2-3 except that H-ZSM-5 (CBV 8014, Zeolyst International, USA) having a Si/Al$_2$ molar ratio of 80 was used in Example 2-3.

Compositions of the ethanol dehydration catalysts according to the examples and comparative examples are listed in Table 1 below.

TABLE 1

| Category | Si/Al$_2$ molar ratio | La content (wt %) | P content (wt %) | Ga content (wt %) |
|---|---|---|---|---|
| Example 1-1 | 30 | 0.1 | — | — |
| Example 1-2 | 30 | 0.25 | — | — |
| Example 1-3 | 30 | 0.5 | — | — |
| Example 1-4 | 30 | 0.5 | 0.5 | — |
| Example 1-5 | 30 | 0.5 | 1 | — |
| Example 1-6 | 23 | 0.25 | — | — |
| Comparative Example 1-1 | 30 | — | — | — |
| Comparative Example 1-2 | 30 | 1 | — | — |
| Comparative Example 1-3 | 30 | 2 | — | — |
| Comparative Example 1-4 | 30 | — | 2 | — |
| Comparative Example 1-5 | 30 | 0.5 | 2 | — |
| Comparative Example 1-6 | 50 | 0.25 | — | — |
| Comparative Example 1-7 | 80 | 0.25 | — | — |
| Example 2-1 | 30 | — | — | 0.05 |
| Example 2-2 | 30 | — | — | 0.1 |
| Example 2-3 | 30 | — | — | 0.25 |
| Example 2-4 | 30 | — | — | 0.5 |
| Example 2-5 | 30 | — | — | 0.75 |
| Example 2-6 | 30 | — | — | 1 |
| Example 2-7 | 30 | 0.25 | — | 0.25 |
| Example 2-8 | 30 | 0.25 | — | 0.5 |
| Example 2-9 | 23 | — | — | 0.25 |
| Comparative Example 2-1 | 30 | — | — | 0.02 |
| Comparative Example 2-2 | 30 | — | — | 1.25 |
| Comparative Example 2-3 | 30 | 0.25 | — | 0.75 |
| Comparative Example 2-4 | 30 | 0.75 | — | 0.25 |
| Comparative Example 2-5 | 50 | — | — | 0.25 |
| Comparative Example 2-6 | 80 | — | — | 0.25 |

Experimental Example 1: Characterization of Ethanol Dehydration Catalyst (1) Pore Analysis of Ethanol Dehydration Catalyst In order to confirm pore characteristics of the ethanol dehydration catalyst according to the present invention, nitrogen adsorption and desorption experiments of the ethanol dehydration catalysts prepared according to Examples 1-1 to 1-3 and Comparative Examples 1-1 to 1-5 and the ethanol dehydration catalysts prepared according to Examples 2-2, 2-3, 2-4, and 2-7 and Comparative Examples 2-2 and 2-3 were performed, and Brunauer, Emmett and Teller (BET) surface area and fine pore volume were measured. The following Table 2 lists the results measured using a BET surface area analyzer (BELSORP-max, BEL Japan Inc.).

TABLE 2

| Category | BET surface area (m$^2$/g) | Fine pore volume (cm$^3$/g) |
|---|---|---|
| Example 1-1 | 511.2 | 0.220 |
| Example 1-2 | 406.8 | 0.174 |
| Example 1-3 | 403.8 | 0.172 |
| Comparative Example 1-1 | 397.7 | 0.171 |
| Comparative Example 1-2 | 383.8 | 0.166 |
| Comparative Example 1-3 | 355.7 | 0.150 |
| Comparative Example 1-4 | 391.8 | 0.160 |
| Comparative Example 1-5 | 401.6 | 0.158 |
| Example 2-2 | 417.5 | 0.189 |
| Example 2-3 | 401.0 | 0.183 |
| Example 2-4 | 377.4 | 0.172 |
| Example 2-7 | 423.3 | 0.216 |
| Comparative Example 2-2 | 350.1 | 0.135 |
| Comparative Example 2-3 | 403.0 | 0.209 |

Referring to Table 2, it may be understood that relative BET surface area and fine pore volume were significantly increased when the lanthanum was introduced into the ethanol dehydration catalyst, but the BET surface area and fine pore volume were slightly decreased as the lanthanum content increased, and, in a case in which phosphorous was introduced, it may be understood that the BET surface area was decreased and the fine pore volume was also slightly decreased (see Examples 1-1 to 1-3 and Comparative Examples 1-1 to 1-5). It may be considered that this was caused by an effect of partial clogging of the pores of the catalyst.

Also, it may be understood that the BET surface area and fine pore volume were significantly increased when the gallium was introduced into the ethanol dehydration catalyst in an amount of 0.1 wt %, but the BET surface area and fine pore volume were slightly decreased as the gallium content increased. Furthermore, it may be understood that the increases in the BET surface area and the fine pore volume were much more pronounced when the lanthanum was introduced, but the BET surface area and fine pore volume were decreased as the amount of the introduced gallium was increased (see Examples 2-2, 2-3, 2-4, and 2-7 and Comparative Examples 2-2 and 2-3). It may be considered that this was also caused by the effect of partial clogging of the pores of the catalyst.

The BET surface areas of the prepared catalysts were in a range of 200 m$^2$/g to 600 m$^2$/g, wherein, in a case in which the BET surface area was less than 200 m$^2$/g, the activity may be reduced because a severe pore clogging phenomenon may occur due to the additives, and in a case in which the BET surface area was greater than 600 m$^2$/g, it may be considered that structural breakage occurred during a preparation process for controlling the acidity of the catalyst.

(2) Effects of Lanthanum and Gallium on Crystal Structure of Ethanol Dehydration Catalyst In order to investigate effects of lanthanum and gallium on a crystal structure of the ethanol dehydration catalyst according to the present invention, X-ray diffraction (XRD, Empyrean, PANalytic B. V., Netherlands) analysis of the ethanol dehydration catalysts prepared according to Examples 1-1 to 1-3 and Comparative Examples 1-1 and 1-2 and the ethanol dehydration catalysts prepared according to Examples 2-3, 2-4, 2-6, 2-7, and 2-8 and Comparative Example 1-1 were performed, and the results thereof are respectively presented in FIGS. 1 and 2.

First, referring to FIG. 1, disappearance of characteristic peaks of H-ZSM-5 (see Comparative Example 1-1) or an unusual peak was not observed, but it was observed that strengths of peaks at 2θ=22 to 25 were reduced with respect to the catalysts in which lanthanum was introduced in an amount of 0.5 wt % or more. It may be estimated that this is due to a cation structure distribution having the form of La(OH)$_2^+$ instead of La(OH)$^{2+}$ with respect to the H-ZSM-5 with a high density of alumina. Thus, it may be considered that an optimum point of composition, which did not degrade the dehydration performance of the H-ZSM-5 and was effective in preventing dealumination through the strengthening of the crystal structure, was in a range in which the lanthanum content was not greater than 0.5 wt %.

Figure 2:
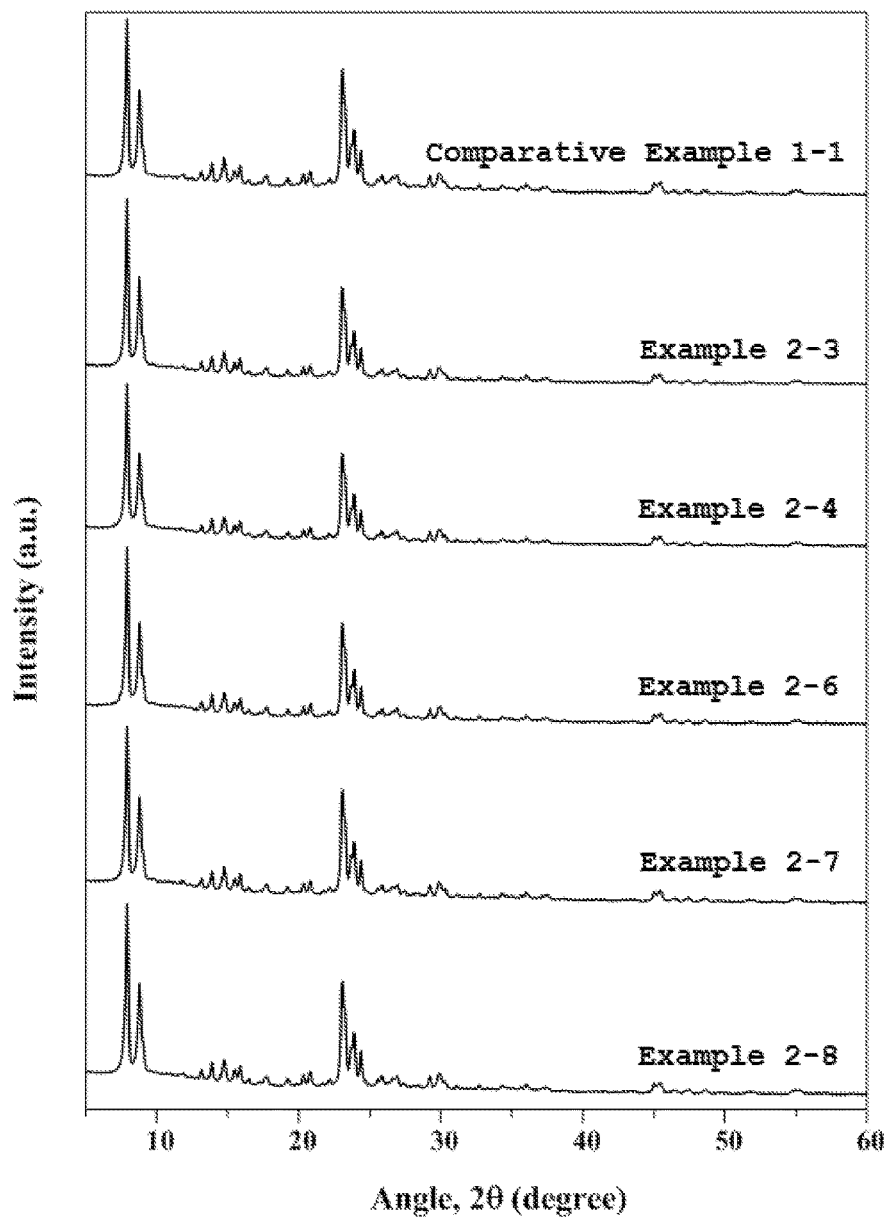
FIG. 2 a graph illustrating results of X-ray diffraction analysis of ethanol dehydration catalysts prepared according to Examples 2-3, 2-4, 2-6, 2-7, and 2-8 and Comparative Example 1-1 of the present invention.

Next, referring to FIG. 2, since the disappearance of the characteristic peaks of the H-ZSM-5 (see Comparative Example 1-1) or an unusual peak was not observed with respect to the catalysts into which gallium was introduced, it may be considered that deformation of the structure of the H-ZSM-5 did not occur.

Experimental Example 2: Analysis of Catalytic Activity and Yield of Ethylene by Ethanol Dehydration Using Ethanol Dehydration Catalyst into which Lanthanum or Gallium was Introduced The following preparation reaction was performed to analyze the yield of ethylene by ethanol dehydration using the ethanol dehydration catalyst according to the present invention.

Preparation Reaction Example

With respect to the ethanol dehydration, the performance of the catalyst was evaluated using a fixed bed reactor. 0.2 g of each of the catalysts for ethanol dehydration prepared according to the examples and comparative examples was filled in a quartz reactor, and nitrogen and ethanol were introduced as reactants into a catalyst layer to prepare ethylene. The nitrogen was used as a carrier, a flow rate was 50 sccm, and a flow rate of the ethanol was set to 0.020 ml/min by using a pump for high performance liquid chromatography (HPLC) (WHSV=5 hr$^{-1}$). The reaction pressure was atmospheric pressure, and dehydration was performed by supplying ethanol at a time when the reaction temperature was constantly controlled. The ethanol used as a raw material was Brazilian sugarcane-derived hydrous ethanol (ethanol content of 95%). Analysis of reaction products outlet from the reactor was performed hourly and the reaction products were quantified by gas chromatography equipped with a 10-port valve for on-line compositional analysis. First, ethanol conversion rate for each reaction temperature and ethylene selectivity of H-ZSM-5 (Comparative Example 1-1), as a basic catalyst, were measured, and the results thereof are presented in Table 3 below. Ethanol conversion rates and ethylene selectivities of the catalysts according to the other examples and comparative examples at a reaction temperature of 240° C. were measured, and the results thereof are presented in Table 4 below. Herein, the ethanol conversion rate and the ethylene selectivity were calculated by the following Equations 1 and 2. Also, the reaction results were based on results obtained after 11.5 hours after the start of the reaction.

$$\text{Ethanol conversion rate (\%)} = \frac{\text{number of moles of ethanol converted to product}}{\text{number of moles of ethanol supplied}} \times 100 \quad \text{[Equation 1]}$$

$$\text{Ethylene selectivity (\%)} = \frac{\text{number of moles converted to ethylene}}{\text{number of moles of ethanol converted to product}} \times 100 \quad \text{[Equation 2]}$$

TABLE 3

| Reaction temperature (° C.) | Conversion rate (%) | Selectivity (%) | | | |
|---|---|---|---|---|---|
| | | Ethylene | DEE | Acetate | Other hydrocarbons |
| 200 | 17.0 | 13.7 | 77.2 | 1.2 | 7.9 |
| 220 | 65.6 | 54.1 | 41.5 | 0.1 | 4.3 |
| 240 | 90.4 | 93.7 | 1.4 | 0.0 | 4.9 |
| 260 | 99.8 | 94.3 | 0.2 | 0.0 | 5.5 |
| 280 | 99.6 | 87.6 | 0.1 | 0.0 | 12.3 |
| 300 | 99.7 | 78.2 | 0.0 | 0.0 | 21.8 |

TABLE 4

| Category | Conversion rate (%) | Selectivity (%) | | | |
|---|---|---|---|---|---|
| | | Ethylene | DEE | Acetate | Other hydrocarbons |
| Example 1-1 | 95.4 | 95.8 | 1.3 | 0.0 | 2.9 |
| Example 1-2 | 99.5 | 98.4 | 0.0 | 0.0 | 1.6 |
| Example 1-3 | 98.4 | 98.1 | 0.3 | 0.0 | 1.6 |
| Example 1-4 | 95.2 | 97.4 | 0.9 | 0.0 | 1.7 |
| Example 1-5 | 94.7 | 95.4 | 1.7 | 0.1 | 2.8 |
| Example 1-6 | 98.3 | 98.4 | 0.2 | 0.0 | 1.4 |
| Comparative Example 1-2 | 85.8 | 71.6 | 27.4 | 0.0 | 1.0 |
| Comparative Example 1-3 | 84.0 | 66.7 | 32.7 | 0.0 | 0.7 |
| Comparative Example 1-4 | 83.3 | 39.9 | 59.7 | 0.0 | 0.4 |
| Comparative Example 1-5 | 82.5 | 43.1 | 56.5 | 0.0 | 0.4 |
| Comparative Example 1-6 | 85.7 | 75.3 | 20.8 | 0.0 | 3.9 |
| Comparative Example 1-7 | 78.2 | 68.5 | 28.1 | 0.0 | 3.4 |
| Example 2-1 | 99.6 | 95.1 | 0.1 | 0.0 | 4.9 |
| Example 2-2 | 99.6 | 96.9 | 0.1 | 0.0 | 3.0 |
| Example 2-3 | 99.5 | 98.0 | 0.0 | 0.0 | 2.0 |
| Example 2-4 | 99.4 | 97.1 | 0.0 | 0.0 | 2.9 |
| Example 2-5 | 99.6 | 94.3 | 0.0 | 0.0 | 5.7 |
| Example 2-6 | 99.9 | 91.7 | 0.1 | 0.0 | 8.2 |
| Example 2-7 | 99.9 | 97.4 | 0.0 | 0.0 | 2.6 |
| Example 2-8 | 99.6 | 97.1 | 0.1 | 0.0 | 2.8 |
| Example 2-9 | 98.1 | 95.4 | 0.1 | 0.0 | 4.5 |
| Comparative Example 2-1 | 93.6 | 94.1 | 0.7 | 0.0 | 5.2 |
| Comparative Example 2-2 | 94.8 | 37.6 | 2.3 | 1.4 | 58.7 |
| Comparative Example 2-3 | 88.7 | 82.8 | 1.5 | 0.4 | 15.3 |
| Comparative Example 2-4 | 89.6 | 75.1 | 16.2 | 0.2 | 8.5 |
| Comparative Example 2-5 | 86.3 | 92.8 | 0.8 | 0.1 | 6.3 |
| Comparative Example 2-6 | 77.1 | 61.4 | 22.5 | 0.0 | 16.1 |

First, as illustrated in Table 3, as a result of the investigation of the basic catalyst for each reaction temperature, it may be confirmed that the H-ZSM-5 having a Si/Al$_2$ molar ratio of 30 exhibited the highest ethanol conversion rate and ethylene selectivity at 260° C. At a reaction temperature of less than 260° C., diethylene ether (DEE) was produced with the reduction of the conversion rate, and, at a reaction temperature of greater than 260° C., although a high conversion rate was maintained, heavy hydrocarbons including an aromatic group was dominantly produced.

Table 4 illustrates the measurement results of ethanol conversion rates and ethylene selectivities of the catalysts prepared according to the examples and the other comparative examples at a reaction temperature of 240° C. at which the ethanol conversion rate and ethylene selectivity of the basic catalyst were maintained at 90% or more. As a result of comparative experiment on the catalyst according to Non-Patent Document 2 (Nina) (see Comparative Example 1-5), which had been evaluated to have excellent dehydration performance of hydrous ethanol by including lanthanum and phosphorous, and the catalyst according to Non-Patent Document 1 (Zhang) (see Comparative Example 1-4) which had been reported to have a coking suppression effect by including phosphorous, both of the two comparative examples had an ethanol conversion rate of about 83% and an ethylene selectivity of about 40%. However, with respect to the catalysts (Examples 1-1 to 1-3 and 1-6), in which lanthanum was introduced in an amount of 0.1 wt % to 0.5 wt %, and the catalysts (Examples 1-4 and 1-5) in which phosphorous was further introduced in an amount of 1 wt % or less, it may be understood that both of the ethanol conversion rate and the ethylene selectivity were 95% or more and thus, activity was similar to that of the basic catalyst H-ZSM-5. In particular, in a case in which lanthanum was introduced in an amount of about 0.25 wt %, it may be understood that both of the ethanol conversion rate and the ethylene selectivity were 98% or more and thus, very high activity was exhibited. With respect to the catalysts (Comparative Examples 1-6 and 1-7) in which the Si/Al$_2$ molar ratio exceeded an appropriate level, it may be confirmed that since the activity of the catalyst was limited due to the reduction in the density of alumina, the ethanol conversion rate and ethylene selectivity were low.

With respect to the catalysts (Examples 2-1 to 2-6) in which gallium was introduced in an amount of 0.05 wt % to 1 wt %, it may be understood that the conversion rate and selectivity of ethanol were significantly increased in comparison to the starting catalyst H-ZSM-5 (Comparative Example 1-1). It was confirmed that activities of the catalysts within the above composition range all exhibited similar conversion rates of 99% or more, but the selectivity was changed according to the composition. The catalyst (Comparative Example 2-1), in which gallium was introduced in an amount of less than 0.05 wt %, among the catalysts having gallium introduced thereinto tended to have a performance closer to that of the basic catalyst H-ZSM-5 (Comparative Example 1-1), and with respect to the catalyst (Comparative Example 2-2), in which gallium was introduced in an amount of greater than 1 wt %, the selectivity of ethylene was significantly reduced so that heavy hydrocarbons including an aromatic compound were produced. Non-Patent Documents 4 and 5 disclose that it is effective in increasing the selectivity of the aromatic compound when the catalysts are prepared such that ZSM-5 is used as a starting catalyst and the amount of gallium is maintained at an amount of 2 wt % or more, and it may be considered that it was in good agreement with qualitative characteristics distinguished when comparing the performance of the catalyst prepared according to Comparative Example 3 with the performances of the catalysts prepared according to Examples 2-1 to 2-6. The above-described prior patent of the present inventors discloses that the introduction of lanthanum into H-ZSM-5 is effective in the preparation of ethylene through dehydration of ethanol. In particular, when the lanthanum was introduced in an amount of 0.25 wt %, performance (or yield) and stability (or long lifetime of the catalyst) were excellent. In order to identify whether additional introduction of gallium was effective when La-ZSM-5 (Example 1-2), in which lanthanum was introduced in an optimum composition (0.25 wt %), was used as a basic catalyst instead of using the H-ZSM-5 (Comparative Example 1-1), performances of the catalysts were evaluated by changing the metal-containing composition as in Examples 2-7 and 2-8 and Comparative Examples 2-3 and 2-4. It was observed that, with respect to the catalyst prepared by using the La-ZSM-5 (0.25 wt %) as a starting catalyst, the selectivity was slightly reduced and the conversion rate was slightly increased in comparison to the catalysts (Examples 2-3 and 2-4) prepared by using the H-ZSM-5 as a starting catalyst. With respect to the catalysts (Comparative Examples 2-3 and 2-4) in which a total amount of metal introduced was 1 wt % or more by increasing the amount of gallium or the amount of lanthanum, the ethanol conversion rates and the ethylene selectivities were significantly reduced to 90% or less. This indicated that the total amount of the introduced metal as well as the optimum combination of components must be adjusted in order to prepare ethylene in high yield through the dehydration of ethanol.

In order to confirm whether the ethanol dehydration catalyst, in which lanthanum and/or gallium was introduced, according to the present invention may prepare ethylene in high yield without deactivation for a long time, long-life test of the catalyst was performed in which ethanol conversion rate and ethylene selectivity were measured hourly up to 240 hours after the start of the dehydration by using each of catalysts prepared according to Examples 1-2 and 1-3 and Comparative Example 1-1 and the catalysts (Examples 2-3 and 2-7) seemed to have the best performance in the performance evaluation of catalysts after 11.5 hours among the ethanol dehydration by using H-ZSM-5 and ZSM-5 having a trace amount of lanthanum introduced thereinto as starting catalysts and introducing gallium, and the results thereof are presented in Table 5 below.

TABLE 5

| Category | Reaction time (hr) | Conversion rate (%) | Selectivity (%) | | | |
|---|---|---|---|---|---|---|
| | | | Ethylene | DEE | Acetate | Other hydrocarbons |
| Example 1-2 | 5 | 99.5 | 98.1 | 0.1 | 0.0 | 1.7 |
| | 24 | 98.3 | 98.7 | 0.1 | 0.0 | 1.2 |
| | 48 | 99.7 | 97.9 | 0.0 | 0.0 | 2.1 |
| | 72 | 99.1 | 98.8 | 0.0 | 0.0 | 1.2 |
| | 96 | 99.6 | 98.0 | 0.0 | 0.0 | 1.9 |
| | 120 | 99.3 | 98.5 | 0.0 | 0.1 | 1.4 |

TABLE 5-continued

| Category | Reaction time (hr) | Conversion rate (%) | Selectivity (%) | | | |
|---|---|---|---|---|---|---|
| | | | Ethylene | DEE | Acetate | Other hydrocarbons |
| | 144 | 99.7 | 98.1 | 0.0 | 0.1 | 1.8 |
| | 168 | 99.6 | 98.0 | 0.0 | 0.1 | 1.9 |
| | 192 | 99.7 | 98.6 | 0.0 | 0.0 | 1.4 |
| | 216 | 99.4 | 98.2 | 0.0 | 0.0 | 1.7 |
| | 240 | 99.5 | 98.3 | 0.0 | 0.1 | 1.6 |
| Example 1-3 | 5 | 98.7 | 97.9 | 0.2 | 0.0 | 1.8 |
| | 24 | 96.4 | 97.3 | 1.5 | 0.0 | 1.2 |
| | 48 | 99.1 | 97.9 | 0.1 | 0.0 | 1.9 |
| | 72 | 97.5 | 98.1 | 0.4 | 0.0 | 1.5 |
| | 96 | 98.6 | 97.9 | 0.2 | 0.1 | 1.9 |
| | 120 | 98.4 | 98.4 | 0.2 | 0.0 | 1.4 |
| | 144 | 97.9 | 97.9 | 0.2 | 0.0 | 1.8 |
| | 168 | 98.9 | 98.3 | 0.1 | 0.0 | 1.6 |
| | 192 | 98.7 | 98.0 | 0.1 | 0.0 | 1.9 |
| | 216 | 98.3 | 98.1 | 0.3 | 0.1 | 1.6 |
| | 240 | 98.2 | 98.1 | 0.3 | 0.1 | 1.5 |
| Example 2-3 | 5 | 99.8 | 96.4 | 0.02 | 0.0 | 3.6 |
| | 24 | 99.8 | 97.4 | 0.02 | 0.0 | 2.6 |
| | 48 | 99.8 | 97.4 | 0.02 | 0.0 | 2.6 |
| | 72 | 99.4 | 98.0 | 0.01 | 0.0 | 1.9 |
| | 96 | 99.8 | 97.5 | 0.04 | 0.0 | 2.4 |
| | 120 | 99.4 | 98.1 | 0.01 | 0.0 | 1.9 |
| | 144 | 99.8 | 97.6 | 0.02 | 0.0 | 2.3 |
| | 240 | 99.1 | 96.1 | 0.2 | 0.0 | 3.7 |
| Example 2-7 | 5 | 99.8 | 97.1 | 0.02 | 0.0 | 2.8 |
| | 24 | 99.9 | 96.8 | 0.02 | 0.0 | 3.1 |
| | 48 | 99.8 | 97.7 | 0.01 | 0.0 | 2.2 |
| | 72 | 99.8 | 97.2 | 0.01 | 0.0 | 2.7 |
| | 96 | 99.8 | 97.6 | 0.02 | 0.0 | 2.3 |
| | 120 | 99.8 | 98.0 | 0.01 | 0.0 | 1.9 |
| | 144 | 99.9 | 97.4 | 0.01 | 0.0 | 2.5 |
| | 240 | 99.7 | 97.7 | 0.1 | 0.0 | 2.2 |
| Comparative Example 1-1 | 0.5 | 91.3 | 94.6 | 1.4 | 0.0 | 5.8 |
| | 35 | 73.1 | 58.1 | 23.1 | 0.2 | 18.6 |
| | 70 | 62.4 | 48.1 | 36.2 | 0.4 | 15.3 |

Referring to Table 5, with respect to the catalysts (Examples 1-2 and 1-3) in which the amount of lanthanum was introduced within the optimum range according to the present invention, since 98% or more of the ethanol conversion rate and 98% or more of the ethylene selectivity may be maintained for 240 hours or more when an ethanol feedstock was supplied at a space velocity (WHSV) of 5 hr$^{-1}$, it may be confirmed that the performances of the catalysts may be maintained for a long time while being much better than the initial activity of the basic catalyst (Comparative Example 1-1). In particular, it may be understood that the performances of the catalysts after 70 hours showed a notable difference.

Also, in a case where the catalysts (Examples 2-3 and 2-7), in which the amount of gallium was introduced within the optimum range, according to the present invention was used, it was confirmed that 99% or more of the ethanol conversion rate and 96% to 98% of the ethylene selectivity, which were measured at almost all time points, were maintained for 240 hours or more when the ethanol feedstock was supplied at a space velocity (WHSV) of 5 hr$^{-1}$.

In order to identify the effect of the reaction temperature on the performance of two catalysts (Examples 2-3 and 2-4) which exhibited the best performance among the catalysts in which H-ZSM-5 was used as a starting catalyst and different amounts of gallium were introduced, ethanol conversion rates and ethylene selectivities after 11.5 hours were measured, and the results thereof are presented in Table 6 below.

TABLE 6

| Category | Reaction temperature (° C.) | Conversion rate (%) | Selectivity (%) | | | |
|---|---|---|---|---|---|---|
| | | | Ethylene | DEE | Acetate | Other hydrocarbons |
| Example 2-3 | 200 | 81.2 | 70.9 | 28.3 | 0.0 | 0.7 |
| | 230 | 98.0 | 98.1 | 0.05 | 0.0 | 1.8 |
| | 235 | 99.2 | 98.0 | 0.01 | 0.0 | 1.9 |
| | 240 | 99.5 | 98.0 | 0.01 | 0.0 | 2.2 |
| | 260 | 99.9 | 86.8 | 0.3 | 0.1 | 12.6 |
| Example 2-4 | 200 | 86.1 | 93.9 | 0.03 | 0.0 | 6.0 |
| | 230 | 92.5 | 96.9 | 1.5 | 0.0 | 1.5 |
| | 235 | 95.0 | 97.1 | 0.05 | 0.0 | 2.7 |
| | 240 | 98.4 | 96.9 | 0.06 | 0.0 | 3.0 |
| | 260 | 99.9 | 89.3 | 0.2 | 0.05 | 10.4 |

As illustrated in Table 6, with respect to the catalyst (Example 2-3) in which gallium was introduced in an amount of 0.25 wt %, it was observed that both of the conversion rate and selectivity were 98% or more in a reaction temperature range of 230° C. to 240° C., but, with respect to the catalyst (Example 2-4) in which gallium was introduced in an amount of 0.5 wt %, relatively high conversion rate and selectivity were observed only in a very narrow temperature region near 240° C.

While the present invention has been particularly shown and described with reference to preferred embodiments thereof, it will be understood by those skilled in the art that various modifications and changes in form and details may be made therein without departing from the spirit and scope of the invention as defined by the appended claims.

The invention claimed is:

1. An ethanol dehydration catalyst for converting a feedstock comprising anhydrous ethanol or hydrous ethanol to ethylene, wherein the catalyst comprises 0.1 wt % to 0.5 wt % of lanthanum (La) in ZSM-5 and 0.01 wt % to 1 wt % of phosphorous (P), wherein the wt % of the lanthanum and the wt % of the phosphorous are each determined with respect to a weight of the catalyst, wherein the ZSM-5 has a silica to alumina molar ratio of 20 to 45, wherein the hydrous ethanol has a water content of 30 wt % or less with respect to a weight of the feedstock, and wherein the catalyst has an ethanol conversion rate of 98% or more and an ethylene selectivity of 98% or more, the ethanol conversion rate and the ethylene selectivity being measured after dehydration at a weight hourly space velocity (WHSV) of 5 $hr^{-1}$ and a temperature of 240° C. for 240 hours.

* * * * *